United States Patent [19]

Bell et al.

[11] 4,237,063

[45] Dec. 2, 1980

[54] SYNTHESIS GAS CONVERSION

[75] Inventors: Weldon K. Bell, Pennington; Clarence D. Chang, Princeton, both of N.J.

[73] Assignee: Mobil Oil Corporation, New York, N.Y.

[21] Appl. No.: 41,956

[22] Filed: May 23, 1979

Related U.S. Application Data

[63] Continuation-in-part of Ser. No. 896,542, Apr. 14, 1978, abandoned.

[51] Int. Cl.³ .......................... C07C 1/02; C07C 1/04; C07C 27/06
[52] U.S. Cl. .......................... 260/449 R; 260/449.6 R; 260/449 M; 260/449.6 M; 260/449.5; 252/438; 252/455.2
[58] Field of Search .................... 260/449 R, 449.6 R, 260/449.6 M, 449.5

[56] References Cited

U.S. PATENT DOCUMENTS 4,086,262   4/1948   Chang et al. ..................... 260/449.6

FOREIGN PATENT DOCUMENTS

| 847334 | 4/1977 | Belgium | 260/449.6 |
| 300294 | 11/1928 | United Kingdom | 260/449.6 |
| 317808 | 8/1929 | United Kingdom | 260/449.6 |

*Primary Examiner*—Howard T. Mars
*Attorney, Agent, or Firm*—Charles A. Huggett; Raymond W. Barclay

[57] ABSTRACT

Synthesis gas is converted to valuable hydrocarbon or alcohol products over catalysts comprising metal cyanide complexes which have been activated by treatment with a reducing gas. The metal cyanide catalysts of this invention, when compared to prior art catalysts, demonstrate increased water gas shift activity such that more oxygen is rejected from the process as $CO_2$ rather than $H_2O$, thus improving the economics of the synthesis gas conversion process.

7 Claims, 1 Drawing Figure

1

SYNTHESIS GAS CONVERSION

CROSS REFERENCE TO RELATED APPLICATIONS

This is a continuation in part of copending application Ser. No. 896,542, filed Apr. 14, 1978, now abandoned.

BACKGROUND OF THE INVENTION

1. Field of the Invention

This invention relates to an improved process for the conversion of synthesis gas, i.e. mixtures of gaseous carbon oxides with hydrogen or hydrogen donors, to valuable hydrocarbon or alcohol products, particularly gasoline or methanol.

In one aspect, this invention is particularly concerned with a process for converting synthesis gas to hydrocarbon mixtures rich in aromatics.

In another aspect, this invention is concerned with providing novel catalysts for the conversion of synthesis gas to hydrocarbon mixtures.

In yet another aspect, this invention is concerned with catalysts which exhibit increased water gas shift activity so that greater amounts of oxygen are rejected from the process as $CO_2$ rather than as $H_2O$.

2. Description of the Prior Art

With the forecasted exhaustion of the crude petroleum resources of this country drawing nearer and nearer, increasing thought must be given to utilizing the existing vast coal reserves as a major source of energy. However, since the present energy requirements are based primarily on liquid fuels, especially gasoline, methods must be found to convert coal into usable liquid fuels if it is to become a major energy source.

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. Although various processes may be employed for the gasification, those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels, is given in Encyclopedia of Chemical Technology, Edited by Kirk-Othmer, Second Edition, Volume 10, pages 353–433, (1966), Interscience Publishers, New York, New York, the contents of which are herein incorporated by reference. The techniques for gasification of coal or other solid, liquid or gaseous fuel are not considered to be per se inventive here.

It would be very desirable to be able to effectively convert synthesis gas, and thereby coal and natural gas, to highly valued hydrocarbons such as motor gasoline with high octane number, petrochemical feedstocks, liquifiable petroleum fuel gas, and aromatic hydrocarbons. It is well known that synthesis gas will undergo conversion to form reduction products of carbon monoxide, such as hydrocarbons, at from about 300° F. to about 850° F. under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. The types of catalysts that have been studied for this and related processes include those based on metals or oxides of iron, cobalt, nickel, ruthenium, thorium, rhodium and osmium.

The wide range of catalysts and catalyst modifications disclosed in the art and an equally wide range of conversion conditions for the reduction of carbon monoxide by hydrogen provide considerable flexibility toward obtaining selected boiling-range products. Nevertheless, in spite of this flexibility, it has not proved possible to make such selections so as to produce liquid hydrocarbons in the gasoline boiling range which contain highly branched paraffins and substantial quantities of aromatic hydrocarbons, both of which are required for high quality gasoline, or to selectively produce aromatic hydrocarbons particularly rich in the benzene to xylenes range. A review of the status of this art is given in "Carbon Monoxide-Hydrogen Reactions," Encyclopedia of Chemical Technology, Edited by Kirk-Othmer, Second Edition, Volume 4, pp. 446–488, Interscience Publishers, New York, N.Y., the text of which is incorporated herein by reference.

McGrath, in U.S. Pat. Nos. 2,637,739 and 2,754,314 teaches that metals or the oxides of metals in Group VIII of the Periodic Table can be employed, either alone or in combination with supporting materials, as catalysts for the Fischer-Tropsch conversion.

In U.S. Pat. No. 3,013,990, Breck discloses Fischer-Tropsch catalysts which comprise a zeolite molecular sieve containing iron, nickel, cobalt or oxides thereof in the internal absorption area of the zeolite molecular sieve. The use of natural zeolite molecular sieves such as chabazite, faujasite, erionite, mordenite, gmelinite, and the calcium form of analcite; as well as synthetic molecular sieves such as zeolites A, D, L, R, S, T, X and Y are taught by Breck. The metallic compounds are incorporated in the zeolite by ion exchange methods. None of these references disclose or suggest the transition metal cyanide complexes utilized as the catalysts of the present invention.

The following three patents describe processes and catalysts for the production of ammonia. They contain no disclosure or suggestion of the process of the present invention, i.e., conversion of synthesis gas to valuable hydrocarbon products, nor do they disclose the catalyst compositions or the methods of activation of the present invention.

Starke, in U.S. Pat. No. 1,306,862 describes the catalytic production of ammonia and cyanogen ($C_2N_2$). The catalyst disclosed therein comprises an iron group metal, an alkaline earth metal (Group IIA of Periodic Table) and an alkali metal (Group IA of Periodic Table) and may be formed by mixing "sodium or potassium ferrocyanid" with "calcium or magnesium ferrocyanid" and subjecting those materials to decomposition at high temperatures, ranging between 1500° and 1900° F., in the presence of gaseous mixtures. A suitable gaseous mixture is 10% atmospheric air and 90% producer gas.

U.S. Pat. No. 1,363,392 of Clancy discloses a catalytic method for the synthesizing of ammonia from its elements. The catalyst is prepared by depositing calcium, barium, strontium or potassium "ferro- or ferri-cyanids" on a suitable support and heating in an atmosphere of nitrogen, hydrogen, or mixtures thereof.

In U.S. Pat. No. 1,439,291, also of Clancy, "alkaline metal cyanogen compounds" are activated for the production of ammonia by heating in the presence of ammonia gas. Examples of suitable cyanogen compounds are: $K_4Cr(CN)_6$; $K_3Cr(CN)_6$ $CoCa[Fe(CN)_6]_2$, $K_3Mn(CN)_6$, $Ba_2Mn(CN)_6$, $K_4Mn(CN)_6$, $K_4Ce(CN)_6$ and $Sr_2Ti(CN)_6$. None of the above references disclose or suggest the transition metal cyanide complexes utilized as the novel catalysts of this invention. Nor do they disclose the method of activating said catalysts. In addition, the above references do not teach that any of the catalysts disclosed therein are usable for the conversion of synthesis gas to valuable hydrocarbon or alcohol products.

Recently it has been discovered that synthesis gas may be first converted to oxygenated organic compounds and these then converted to higher hydrocarbons, particularly high octane gasoline, by catalytic contact of the synthesis gas with a carbon monoxide reduction catalyst followed by contacting the conversion products so produced with a special type of zeolite catalyst in a separate reaction zone. This two-stage conversion is described in U.S. Pat. No. 3,894,102, the contents of which are incorporated herein by reference. Attempts to convert synthesis gas over X-zeolite, base exchanged with iron, cobalt and nickel, are described in Erdöl and Kohle-Erdgas, Petrochemie: Brennstoff-Chemie, Vol. 25, No. 4 pp. 187–188, April, 1972.

In addition, it has been discovered that valuable hydrocarbon mixtures may be produced by reacting synthesis gas, in the presence of certain heterogeneous catalysts comprising intimate mixtures of two components in which the first component is selected from the class of inorganic substances that have catalytic activity for the reduction of carbon monoxide, and the second component is an acidic crystalline aluminosilicate of which ZSM-5 is typical. Substantial quantities of liquid mixtures which are rich in branched paraffins and aromatic hydrocarbons and eminently suited for making high octane gasoline or petrochemicals are obtained. This development is described completely in U.S. Pat. No. 4,086,262 of Chang et al. (U.S. Application Ser. No. 733,982 filed Oct. 20, 1976), the contents of which are incorporated herein by reference.

SUMMARY OF THE INVENTION

It is an object of the present invention to provide an improved process for converting fossil fuels to a hydrocarbon mixture that contains large quantities of highly desirable constituents. It is a further object of this invention to provide a more efficient method for converting a mixture of gaseous carbon oxides and hydrogen to a mixture of hydrocarbons. It is a further object of this invention to provide an improved process for the conversion of synthesis gas to valuable hydrocarbon products by increasing the water gas shift activity toward oxygen rejection as $CO_2$ rather than $H_2O$. It is a further object of this invention to provide improved catalysts which produce said increased water gas shift activity for the conversion of synthesis gas to valuable hydrocarbon products.

As those skilled in the art will be aware, when synthesis gas, for examples mixtures of CO and $H_2$, is converted to hydrocarbons, typified by repeating —$CH_2$— groups, substantial amounts of oxygen must be rejected from the system. Oxygen can be rejected as either $CO_2$ or $H_2O$, however, in many instances, especially those involving synthesis gas which is deficient in hydrogen, it is preferred that the oxygen be rejected as $CO_2$.

It has now been found that catalysts which are produced from metal cyanide complexes, hereinafter described in greater detail, are particularly useful for the conversion of synthesis gas to valuable hydrocarbon products. Catalysts comprising the metal cyanide complexes effect a water gas shift activity toward oxygen rejection as $CO_2$ which is greater than that exhibited by prior art synthesis gas conversion catalysts, i.e. magnetite. This change in water gas shift activity has an important beneficial effect on the overall economics of the synthesis gas conversion process since rejection of more oxygen as $CO_2$ instead of $H_2O$ greatly decreases the consumption of expensive hydrogen. In addition, the decrease in the partial pressure of $H_2O$ provides for larger catalyst life by reducing deleterious steaming effects.

The metal cyanide complexes according to the present invention which are used as catalysts for the conversion of synthesis gas are described by the formula:

$A_xB_y[M_z(CN)_i(L)_j]\bullet QH_2O$ where M is a metal selected from:

Groups IIIB, IVB, VB, VIB, VIIB, VIII, IB of the Periodic Table plus zinc and oxides thereof;

z is 1 or 2, but preferably is 1; the sum of i plus j is between 2 and 12, however i is at least 1;

A and B are selected from Groups IIIB, IVB, VB, VIB, VIIB, VIII, IB of the Periodic Table plus zinc, aluminum, tin, antimony, lead, bismuth, phosphorus, arsenic, hydrogen, sodium, potassium, rubidium, cesium, magnesium, calcium, strontium and barium;

at least one of A, B or M has activity for reduction of carbon monoxide; x is multiplied by the charge of A plus y multiplied by the charge of B equals the charge on the $[M_z(CN)_i(L)_j]$ anion;

L is a ligand selected from the group consisting of $H_2O$, $NH_3$, NO, H, halogen, oxides of carbon, oxides of sulfur, OH, SCN, amines, phosphines, and organic chelating agents such as oxalate and EDTA;

and Q is between 0 and 14, preferably between 0 and 4.

It will be appreciated that the A, B, and M components of the above metal cyanide complexes may comprise different valence states of the same metal. An illustration of this is ferric ferrocyanide: $Fe_4^{III}[Fe^{II}(CN)_6]_3$.

The preferred metal cyanide complexes are those, according to the above formula, in which M is selected from zinc, iron, cobalt, nickel, ruthenium, rhodium, chromium, iridium, osmium, copper, rhenium, tungstein, titanium, manganese, molybdenum, lanthanum, cerium, and uranium.

A and B are selected from zinc, iron, cobalt, nickel, ruthenium, thorium, rhodium, zirconium, hafnium, chromium, iridium, osmium, copper, ruthenium, tungsten, titanium, manganese, molybdenum, lanthanum, cerium, uranium, hydrogen, sodium, potassium, rubidium, cesium, magnesium, calcium, strontium and barium.

Particularly preferred for the conversion of synthesis gas to hydrogen products or for water-gas shift are the metal ferrocyanides of the formula:

$A_xB_y[Fe(CN)_6]$ where A and B are selected from zinc, iron, cobalt, nickel, ruthenium, thorium, rhodium, zirconium, hafnium, chromium, iridium, osmium, copper, rhenium, tungsten, titanium, manganese, molybdenum, lanthanum, cerium, uranium, hydrogen, sodium, potassium, rubidium, cesium, magnesium, calcium, strontium and barium. Of these, ferric ferrocyanide, $Fe_4^{III}[Fe^{II}(CN)_6]_3$, also known to the art as insoluble Prussian Blue, is the most significant.

Particularly preferred for the conversion of synthesis gas to alcoholic products (including ethers) and hydrocarbons are the cyano cuprates of the formula: $A_xB_y[Cu(CN)_4]$ where the charge on the $Cu(CN)_4$ union of said cuprate is $-3$ where A and B are selected from zinc, iron, cobalt, nickel, ruthenium, thorium, rhodium, zirconium, hafnium, chromium, iridium, osmium, copper, rhenium, tungsten, titanium, manganese, molybdenum, lanthanum, cerium, uranium, hydrogen, sodium, potassium, rubidium, cesium, magnesium, calcium, strontium and barium.

Of these, zinc cyano cuprate is the most significant.

The metal cyanide complexes of this invention may be produced, for example, by dissolving a salt which contains the desired cyanide complex anion in water and adding a compound containing the desired metal cation or cations. The metal cyanide complex precipitates out of the solution, and can be filtered, washed and dried as is known in the art. Texts in this field, in particular The Chemistry of Cyano Complexes of the Transition Metals by A. G. Sharpe (Academic Press, New York, 1976), the contents of which are incorporated by reference, clearly describe and/or cite the techniques of preparing metal-cyanide complexes.

It is an important advantage of the catalysts of the present invention, over the prior art synthesis catalysts such as magnetite, that the present catalysts are prepared by precipitation. This method allows an even deposit of the catalytic material directly onto the catalyst base, substrate or co-catalyst thus resulting in greater surface areas of the metal component.

It has further been discovered that the metal component designated by the letter B in the above formula, may be ion exchanged with other metals. The metal designated in the above formula by the letter A may be added by ion exchange. Techniques for ion exchange of various materials are well known in the art. Generally, a starting metal cyanide having the formula $B_y[M_z(CN)_i]$ is dispersed in water and an excess of a compound containing the desired cation is added. After stirring for $\frac{1}{4}$ to 100 hours, the resulting product which now has the formula $A_xB_y[M_z(CN)_i]$ is separated, washed and dried. It may be possible, if the contacting is carried out for a long enough period of time to completely exchange the B metal component with the A metal component.

The conversion of synthesis gas results in the production of various oxygenated and hydrocarbon products, depending on the particular catalyst and reaction conditions chosen. Products that are formed include methanol, dimethyl ether, acetone, acetic acid, normal propyl alcohol, higher alcohols, methane, gaseous, liquid and solid olefins and paraffins.

The catalysts of this invention may comprise the activated metal cyanide complexes alone or in the presence of supports or binders.

Thus, in one embodiment, the metal cyanide complexes may be produced as described above, pelleted and activated for the conversion of synthesis gas.

In another embodiment the metal cyanide complexes may be combined with a support or base before pelleting and activation. Typical supports include the porous solid refractory inorganic oxides, although other known supports such as kieselghur or clay may effectively be utilized.

The combination of metal cyanide complex with the support or base may simply comprise a mixing of the two components. Preferably, however, the support or base can be introduced into the solution from which the metal cyanide complexes are precipitated. In this manner, the complexes may be precipitated in an even fashion directly onto the catalyst support or base.

Non-limiting examples of catalyst supports include those having a major component of silica or alumina or both, such as for example, alumina, siliceous materials, open lattice clays and crystalline aluminosilicates.

Non-limiting examples of siliceous materials useful as the substrate include silica and combinations thereof with oxides of metals of Groups II-A, III-A, III-B, IV-A, IV-B, and V-B of the Periodic Table, such as, for example, silica-alumina, silica-magnesia, silica-zirconia, silica-thoria, silica-berylia, silica-titania, as well as ternary compositions of silica, such as, for example, silica-alumina-thoria and silica-alumina-zirconia.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

Zeolites useful for the crystalline aluminosilicate component of this invention include the acidic forms of: zeolite X, described in U.S. Pat. No. 2,882,244; zeolite Y, described in U.S. Pat. No. 3,130,007; mordenite; zeolite L, described in U.S. Pat. No. 3,216,789; zeolite T, described in U.S. Pat. No. 2,950,952; and zeolite beta, described in U.S. Pat. No. 3,308,069. The acidic crystalline aluminosilicate component should be in the hydrogen form, or it may be stabilized by ion exchange with rare earth or other metal cations that need not contribute to the carbon monoxide reducing function.

In a preferred embodiment, the metal cyanide complexes may be combined with a specific class of acidic crystalline aluminosilicates. Heterogeneous catalysts which comprise two components intimately mixed, wherein one component is selected from the class of inorganic substances that have catalystic activity for the reduction of carbon monoxide and the other component is an acidic crystalline aluminosilicate typified by the zeolite ZSM-5 are described with more detail in U.S. Pat. No. 4,086,262 of Chang et al. Conversion of synthesis gas over catalysts containing crystalline aluminosilicates of this class produces hydrocarbon products rich in aromatics.

Crystalline Aluminosilicate Zeolites

The crystalline aluminosilicate zeolites utilized herein are members of a novel class of zeolites that exhibits unusual properties. Although these zeolites have unusually low alumina contents, i.e. high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination; a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which, due to pore blockage or to other cause, may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of normal hexane and 3-methylpentane over a small sample, approximately one gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| CAS | C.I. |
| --- | --- |
| ZSM-5 | 8.3 |
| ZSM-11 | 8.7 |
| ZSM-12 | 2 |
| ZSM-35 | 4.5 |
| ZSM-38 | 2 |
| TMA Offretite | 3.7 |
| Beta | 0.6 |
| ZSM-4 | 0.5 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-35, and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

The heterogeneous catalysts may be prepared in various ways. The two components may be separately prepared in the form of catalyst particles such as pellets or extrudates, for example, and simply mixed in the required proportions. The particle size of the individual component particles may be quite small, for example from about 20 to about 150 microns, when intended for use in fluid bed operation; or they may be as large as up to about ½ inch for fixed bed operation. Or, the two components may be mixed as powders and formed into pellets or extrudate, each pellet containing both components in substantially the required proportions. Binders such as clays may be added to the mixture. Alternatively, the component that has catalytic activity for the reduction of carbon monoxide may be formed on the acidic crystalline aluminosilicate component by conventional means such as impregnation of that solid with salt solutions of the desired metals, followed by drying and calcination. Other means for forming the intimate mixture may be used, such as precipitation of the metal cyanide complex in the presence of the acidic crystalline aluminosilicate. Various combinations of the above preparative methods will be obvious to those skilled in the art of catalyst preparation. It should be cautioned, however, to avoid techniques likely to reduce the crystallinity of the acidic crystalline aluminosilicate.

It will be recognized from the foregoing description that the heterogeneous catalysts, i.e., the above-described intimate mixtures, used in the process of this invention, may have varying degrees of intimacy. At one extreme, when using ½ inch pellets of the metal cyanide complex mixed with ½ inch pellets of the acidic crystalline aluminosilicate, substantially all locations within at least one of the components will be within not more than about ½ inch of some of the other component, regardless of the proportions in which the two components are used. With different sized pellets, e.g., ½ inch and ¼ inch, again substantially all locations within at least one of the components will be within not more than about ½ inch of the other component. These examples illustrate the lower end of the degree of intimacy required for the practice of this invention. At the other extreme, one may ball mill together acid crystalline aluminosilicate particles of about 0.1 micron particle size with colloidal metal cyanide complex of similar particle size followed by pelletization. For this case, substantially all the locations within at least one of the components will be within not more than about 0.1 micron of some of the other component. This exemplifies about the highest degree of intimacy that is practical. The degree of intimacy of the physical mixture may also be expressed as the minimum distance of separation of the central points located with the particles of the two components. This will, on average, be represented by one-half the sum of the average particle size for the two components. Thus for the foregoing example illustrating the highest degree of intimacy, the centers of the particles of either of the two components will be separated from the nearest particle of the other component by an average distance of at least about 0.1 micron. The degree of intimacy of the heterogeneous catalyst is largely determined by its method of preparation, but it may be independently verified by physical methods such as visual observations, examination in an ordinary microscope or with an electron microscope, or by electron microprobe analysis.

It will be apparent that the metal cyanide complexes of this invention can be first prepared dried, and then simply mixed with the desired support material. However, it is also contemplated that the support material may be put in a solution containing the cyanide anion, and a metal cationic salt be added to the mixture of support and anion, so that the metal cyanide complex precipitates out directly onto the support. The resulting impregnated material may be filtered, dried and activated to produce a useful catalyst.

The refractory oxide materials described above are generally utilized only as a support or base. However, for the cyanocuprate complexes described above, alumina acts as a catalyst and its presence appears necessary for those complexes to exhibit catalytic activity for the conversion of synthesis gas. The function of alumina in the cyanocuprate catalysts is unknown and represents a surprising criteria, especially since the presence of alumina is not required in order that other cyanide metal complexes, such as ferric ferrocyanide, exhibit catalytic activity.

The form of the catalyst may be such that it can be utilized in either a fluid or fixed bed. For the former, particles of size 20 to 150 microns are generally provided while the catalyst for the latter are usually much larger in size, such as 1/32" up to ½". Fluid catalyst are produced by methods known to the art such as spray drying.

The metal cyanide complexes described herein are activated by treatment with a reducing gas prior to their utilization for the conversion of synthesis gas. For many of the complexes the reducing gas may comprise hydrogen, oxides of carbon, particularly carbon monoxide, or mixtures thereof. Preferred, however, are those reducing gases which contain oxides of carbon.

With respect to the ferric ferrocyanide complex described hereinabove, it has been found that the most effective gases for activation are those reducing gases which contain oxides of carbon. The preferred gases for this application contain both oxides of carbon and hydrogen. Particularly preferred is a gas containing hydrogen and carbon monoxide in a molar ratio of from about 0.5/1 $H_2/CO$ to about 6/1 $H_2/CO$ or greater. Gases with $H_2/CO$ ratios of from 0.5/1 to 2/1 are more particularly preferred, and gases with $H_2/CO$ ratio of from 1/1 to 2/1 are most particularly preferred. In addition, it has been found that treatment with hydrogen gas is insufficient to activate the ferric ferrocyanide catalysts for the conversion of synthesis gas. Since TGA studies show that ferric ferrocyanide decomposes when contacted with hydrogen at temperatures from 200°–1100° F., it is surprising that such decomposition does not result in catalysts which can be utilized for the conversion of synthesis gas.

Other activation techniques, such as pryolysis, i.e. heating in a inert gas, such as helium, at high temperatures followed by reduction also fail to produce active synthesis gas conversion catalysts from the ferric ferrocyanide.

Conditions for activation of the metal cyanide complexes include temperatures from about 100° F. to 1000°

F. and pressures from about ¼ to 200 atm. Preferred are temperatures from about 150° to 700° F. and pressures near atmospheric. Particularly preferred activation temperatures are those associated with mass changes during thermogravitmetric analysis of a given material in the chosen activating gas.

DETAILED DESCRIPTION AND PREFERRED EMBODIMENTS

Figure 1:
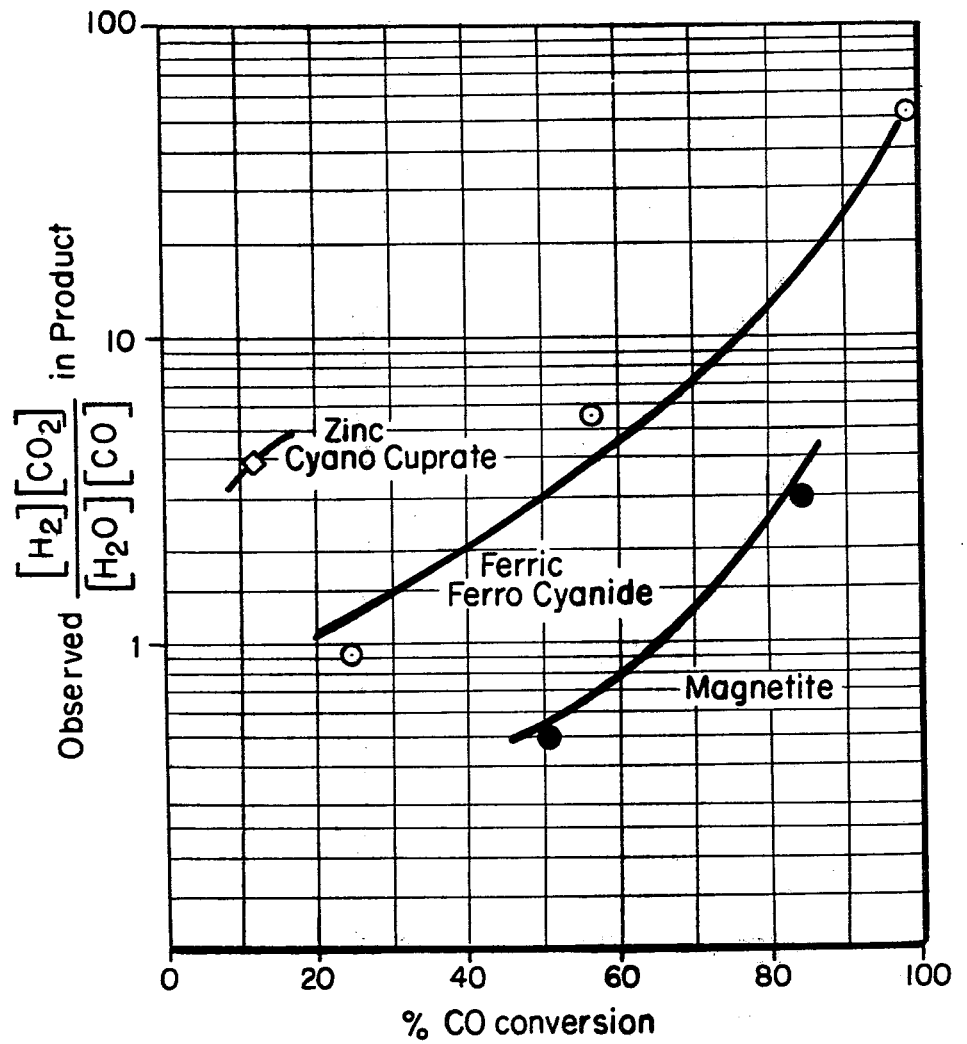

Synthesis gas for use in this invention consists of a mixture of hydrogen gas with gaseous carbon oxides including carbon monoxide and carbon dioxide. By way of illustration, a typical purified synthesis gas will have the composition, on a water-free basis, in volume percentages, as follows: hydrogen, 51; carbon monoxide, 40; carbon dioxide, 4; methane, 1; and nitrogen, 4.

The synthesis gas may be prepared from fossil fuels by any of the known methods, including such in situ gasification processes as the underground partial combustion of coal and petroleum deposits. The term fossil fuels, as used herein, is intended to include anthracite and bituminous coal, lignite, crude petroleum, shale oil, oil from tar sands, natural gas, as well as fuels derived from simple physical separations or more profound transformations of these materials, including coked coal, petroleum coke, gas oil, residua from petroleum distillation, and two or more of any of the foregoing materials in combination. Other carbonaceous fuels such as peat, wood and cellulostic waste materials also may be used.

The raw synthesis gas produced from fossil fuels will contain various impurities such as particulates, sulfur, and metal carbonyl compounds, and will be characterized by a hydrogen-to-carbon oxides ratio which will depend on the fossil fuel and the particular gasification technology utilized. In general, it is desirable for the efficiency of subsequent conversion steps to purify the raw synthesis gas by the removal of impurities. Techniques for such purification are known and are not known and are not part of this invention. Furthermore, should it be required, it is preferred to adjust the hydrogen-to-carbon oxides volume ratio to be within the range of from 0.2 to 6.0 prior to use in this invention. Should the purified synthesis gas be excessively rich in carbon oxides, it may be brought within the preferred range by the well known water-gas shift reaction. On the other hand, should the synthesis gas be excessively rich in hydrogen, it may be adjusted into the preferred range by the addition of carbon dioxide or carbon monoxide. Purified synthesis gas adjusted to contain a volume ratio of hydrogen-to-carbon oxides of from 0.2 to 6.0 will be referred to as adjusted synthesis gas.

It is contemplated that the synthesis gas for use in this invention includes art-recognized equivalents to the already-described described mixtures of hydrogen gas with gaseous carbon oxides. Mixtures of carbon monoxide and steam, for example, or of carbon dioxide and hydrogen, to provide adjusted synthesis gas by in situ reaction, are contemplated. Furthermore, when the novel process of this invention is used to produce hydrocarbon mixtures rich in aromatic hydrocarbons, as will be more fully described, a hydrogen-donor such as methane, methanol, or higher alcohols may be charged with the gaseous carbon oxides mixture to some advantage.

In the process of this invention, synthesis gas is contacted with the catalyst at a temperature of from about 400° F. to 1000° F., preferably from 500° F. to 850° F., at a pressure from 1 to 1000 atmospheres, preferably from 3 to 200 atmospheres, and at a volume hourly space velocity from about 500 to 50,000 volumes of gas, at standard temperature and pressure per volume of catalyst, or equivalent contact time if a fluidized be is used. The catalyst may be contained as a fixed bed, or a fluidized bed may be used. The product stream containing hydrocarbons, unreacted gases and steam may be cooled and the hydrocarbons recovered by any of the techniques known in the art, which techniques do not constitute part of this invention. The recovered hydrocarbons may be further separated by distillation or other means to recover one or more products such as high octane gasoline, propane fuel, benzene, toluene, xylenes, or other aromatic hydrocarbons.

Several experiments were conducted in order to demonstrate the efficacy of the metal cyanide complex materials as catalysts for the conversion of synthesis gas. These experiments are not to be construed as limiting the scope of this invention to the particular metal cyanide complex materials, tests procedures or conversion conditions set forth.

EXAMPLES 1–7

Activation of Ferric Ferrocyanides

These examples illustrate that the ferric ferrocyanide catalysts are not activated for the conversion of synthesis gas by such known activation methods as reduction with hydrogen, pyrolysis, or even pyrolysis followed by treatment with a gas containing $H_2$ and CO. It is surprisingly that activation procedures such as these, which are effective for the activation of Fischer-Tropsch catalysts such as magnetite fail to activate the ferric ferrocyanides. It has been found, however, that treatment with a gas containing $H_2$ and CO is effective for activation of the ferric ferrocyanide complexes.

The catalyst utilized in these examples was a mixture of Prussian Blue, i.e. $Fe_4[Fe(CN)_6]_3$, with a HZSM-5 extrudate in a Fe:HZSM-5 ratio of 1:9, by weight. The HZSM-5 extrudate contained 65% by weight of HZSM-5 and 35% by weight of $Al_2O_3$ and had been precalcined at 1000° F. for 16 hours prior to mixture with the Prussian Blue. The ferric ferrocyanide first was powdered and then mixed with HZSM-5. The mixed powder was then pelleted and broken into particles of 20/30 mesh.

These catalysts were both activated and tested for conversion of synthesis gas in a integral tubular reactor having a length/diameter ratio of about 5. The reaction zone normally contained 3 cc of catalyst. Vycor chips (7 cc) were placed over the catalyst to provide a reactor preheat zone. Temperatures were recorded via an axial thermowell.

Gaseous reactants, at reaction pressure, were filtered through charcoal before being metered through the preheat zone and into the reaction zone.

Reaction products, at reaction pressures, were conducted through an ice bath to remove liquid products. The remaining gases were expanded to room conditions using a back pressure regulator, sampled and metered. The gas phase sample and the condensed liquids were then analyzed by gas chromatography. A material balance, typically taken over a 3-hour period, usually agreed to within 5%.

Activation of the catalyst took place in the aforementioned reaction system by passing an activation gas over the catalyst at activation conditions, i.e. atmospheric pressure and 3000 GHSV for 10 to 16 hours.

Without removing the catalyst, the reactor was flushed with an inert gas and brought to synthesis gas conversion conditions.

The catalysts were then tested for synthesis gas conversion activity and selectivity by introducing a 1:1 molar mixture of $H_2/CO$ at conversion conditions of 28 atmospheric pressure, 600° F. and a WHSV of 10 CO/gFe/hr. Material balances were taken at various times on stream. The results are presented in Table I.

TABLE 1

| Example | 1 | 2 | 3 | 4 | 5 | 6 | 7 |
|---|---|---|---|---|---|---|---|
| Catalyst | ← | ← | Prussian Blue/HZSM-5/Al$_2$O$_3$ | | | → | → |
| Activation Procedure | | | | He at 1100° F. followed by | | | |
| Gas | H$_2$ | H$_2$ | He | He | H$_2$/CO | H$_2$/CO | H$_2$/CO |
| Pressure | 1 atm. | 1 atm. | 1 atm. | 1 atm. | 1 atm. | 1 atm. | 1 atm. |
| Temperature, °F. | 600 | 850 | 1500 | 1100 | 600 | 612 | 600 |
| Activity after 4 hrs. on stream | | | | | | | |
| % CO converted | <.1 inactive | <.1 inactive | <.1 inactive | <.1 inactive | <.1 inactive | 97 | 98 |
| Hydrocarbon Distribution | | | | | | | |
| CH$_4$ | — | — | — | — | — | 28 | 40 |
| C$_2$–C$_4$ Paraffins & Olefins | — | — | — | — | — | 41 | 47 |
| C$_5$ + (PONA) | — | — | — | — | — | 31 | 11 |

Examples 1 and 2 illustrate the ineffectiveness of reduction in hydrogen gas as a technique for activating the ferric ferrocyanides of this invention for the conversion of synthesis gas. Examples, 3, 4 and 5 show that pyrolysis of the ferric ferrocyanide, even if followed by treatment with $H_2/CO$, fails to produce a catalyst active for the conversion of synthesis gas. Finally, Examples 6 and 7 show both the effectiveness of activation with $H_2/CO$ as well as the excellent synthesis gas conversion characteristics of the ferric ferrocyanide catalyst of the invention.

EXAMPLE 8

Surface Area Comparison

The surface area of the ferric ferrocyanide catalyst of the present invention is compared with that of magnetite ($Fe_3O_4$), the closest prior art catalyst.

Ferric ferrocyanide powder (0.56 grams) and magnetite powder (1.59 grams) were each reduced in a high flow of 1 atm. $H_2/CO$ at 580° F. overnight in a surface area apparatus vessel. The reduction was carried out directly in the surface area apparatus vessel to eliminate the possibility of contamination in transferring metals from a separate reduction apparatus to the surface area apparatus. The results showed that magnetite had a surface area of $8 m^2/gm$ while ferric ferrocyanide had surface area of $146 m^2/gm$. Chemical analyses of these reduced materials indicated that the magnetite sample had a carbon content of 5% by weight while the ferric ferrocyanide sample contained 17% carbon by weight. This example shows the significantly different physical properties, i.e. surface area and carbon content, of the ferric ferrocyanide catalyst of the present invention from those of the prior art catalysts.

EXAMPLE 9

Comparison of Water Gas Shift Activity Characteristics

A catalyst containing ferric ferrocyanide on a HZSM-5/alumina base was compared with a magnetite/HZSM-5/alumina catalyst for water gas shift activity. Both catalysts had wt. ratios of Fe/HZSM-5/alumina of 1:9:4.8. The ferrocyanide catalyst was activated in 1 atm. of 1:1 $H_2/CO$ at 620° F. for about 16 hours. The magnetite catalyst was activated in 1 atmosphere of carbon monoxide at 620° F. for about 16 hours. Activation in this gas provided a magnetite catalyst of activity such that conversions similar to those for the ferrocyanide catalyst were obtained.

The catalysts were tested for water gas shift activity at synthesis gas conversion conditions as follows:
Feed $H_2/CO$ (1:1 molar)
Times on Stream 0.1, 1 and 2 days
WHSV 10 gCO/gFe/hr.
Pressure 28 atm.
Temperature 600°–630° F.

The results are plotted in FIG. 1 where the molar concentration of the product stream water gas shift components are expressed as an equilibrium co-efficient and plotted versus CO conversion. The plot shows that the ferric ferrocyanide catalyst provides a closer approach to water gas shift equilibrium than the magnetite catalysts, especially at lower conversions of CO. This is significant in that with this higher degree of internal water gas shift, hydrogen is coproduced thus reducing or eliminating the need for shift of the synthesis gas feed before the reactor. Such catalysts would be expected to accept a synthesis gas feed richer in carbon monoxide from potentially more economical gasifiers.

EXAMPLES 10–12

Effect of Catalyst Base

These examples illustrate that the ferric ferrocyanides are effective catalysts for the conversion of synthesis gas; either alone or in the presence of a number of catalyst bases or co-catalysts. Moreover, the presence or absence of catalyst base or co-catalyst was found not to affect the difference in water gas shift activity from magnetite catalysts, as presented in Example 9.

All of the catalysts tested in this experiment were activated in $H_2/CO$ (1:1 molar) at 1 atm. and 600° F. for about 16 hours.

The synthesis gas conversion was conducted at 28 atm. of a 1:1 molar mix of $H_2/CO$, 600° F. The WHSV was based on gCO/gFe/hr. The results are presented in Table 2.

precipitated material. An x-ray diffraction characterization of this material indicated that a mixture of crystalline phases were probably present.

TABLE 2

| Example | 10 | 11 | 12 |
|---|---|---|---|
| Catalyst | $Fe_4[Fe(CN)_6]$ alone | $Fe_4[Fe(CN)_6]:Al_2O_3$ | $Fe_4[Fe(CN)_6]:HZSM-5$ |
| Proportions | — | $Fe/Al_2O_3 = \frac{1}{4}$ | $Fe/HZSM-5/Al_2O_3 = 1/9/5$ |
| Reaction Conditions, WHSV | 3.6 | 10 | 10 |
| Conversion, Wt. % CO Converted | 92 | 95 | 98 |
| $\frac{[H_2][CO_2]}{[H_2O][CO]}$ | 29 | 16 | 22 |
| Hydrocarbon Distribution, Wt. % | | | |
| $CH_4$ | 16 | 32 | 34 |
| $C_2-C_4$ P + O | 50 | 49 | 37 |
| $C_5^+$ PONA | 34 | 19 | 29 |

Referring to the table, Examples 12 and 13 illustrate the efficacy of the ferric ferrocyanide catalysts in the conversion of synthesis gas either alone or when combined with an alumina catalyst base. A comparison of the water gas shift equilibrium of these two examples with that of Example 14, illustrates that the ferric ferrocyanide and not the presence or absence of a catalyst base or co-catalyst is responsible for the increased water gas shift illustrated in Example 11.

EXAMPLES 13-18

Metal Ferrocyanides

The following examples demonstrate the efficacy of various metal ferrocyanide catalysts for the conversion of synthesis gas. The catalysts were prepared by mixing powdered metal ferrocyanide with a support material, and pelleting, as previously described. These catalysts were activated using $H_2/CO$ (1:1 molar) at 1 atm. and 600° F. for about 16 hours. The catalysts were tested for synthesis gas conversion at 28 atm. of $H_2/CO$ (1:1 molar), 600° F. and 10 WHSV (gCO/gFe/hr.). The results are presented in Table 3.

EXAMPLE 20

The material prepared in Example 19 (15 g) was dispersed in water (50 ml). To this dispersion, a solution of cupric acetate (16.9 g into 1200 ml of water) was added. After one hour of mixing, an olive drab powder was recovered by filtration, washing and vacuum drying. X-ray diffraction of this material indicated an uncharacterized single crystalline species. The Zn/Cu ratio, as determined by x-ray fluorescence was 0.41. This ratio is consistent with a species for which about half of the Zn(II) has been exchanged by Copper (II), i.e. $Cu_{1.5}Zn_{1.5}[Cu(CN)_4]_2$.

EXAMPLE 21

The procedure of Example 20 was repeated, except that contacting was extended to 100 hrs. before filtering. A tan powder with an x-ray diffraction pattern indicating a single uncatalogued crystalline species was recovered. The zinc/copper ratio was estimated to be 0.0005 by x-ray fluoresence. This result is consistent with a species for which all of the zinc was exchanged by Copper(II), i.e. $Cu_3[Cu(CN)_4]_2$.

TABLE 3

| Example | 13 | 14 | 15 | 16 | 17 | 18 |
|---|---|---|---|---|---|---|
| Catalyst | $Mg_2Fe(CN)_6$: HZSM-5: $Al_2O_3$ | $Zn_2Fe(CN)_6$: HZSM-5: $Al_2O_3$ | $Ni_2Fe(CN)_6$: HZSM-5: $Al_2O_3$ | $Co_2Fe(CN)_6$: HZSM-5: $Al_2O_3$ | $Mn_2Fe(CN)_6$: HZSM-5: $Al_2O_3$ | $Cu_2Fe(CN)_6$: $Al_2O_3$ |
| Proportions | ← | $Fe/HZSM-5/Al_2O_3 = 1/9/5$ | | → | → | $Fe/Al_2O_3 = 1/14$ |
| Hours on Stream | 24 | 24 | 29 | 25 | 24* | 99** |
| Conversion, Wt. % converted | 34 | 45 | 37 | 99 | 20 | 93 |
| Hydrocarbon Distribution, Wt. % | | | | | | |
| $CH_4$ | 33 | 35 | 60 | 57 | 11 | 19 |
| $C_2-C_4$ P + O | 29 | 42 | 37 | 31 | 33 | 36 |
| $C_5+$ PONA | 38 | 23 | 3 | 12 | 56 | 45 |

*Activation at 650° F., reaction at 29 atm. and 508° F.
**Activation conducted at 300° F., reaction temperature 600° F. after 96 hours operation at temperatures below 505° F.

EXAMPLE 19

Preparation of $Zn_3[Cu(CN)_4]_2$

Aqueous solutions of $K_3Cu(CN)_4$ and $Zn(OAc)_2$ were prepared by dissolving 28.2 g of CuCN and 61.6 g of KCN into 400 ml of water and 103.8 g of $Zn(OAc)_2$ into 430 ml of water. The solutions were then combined in a stoichiometric amount and a precipitate filtered out, washed with water and collected.

The Zn/Cu (wt) ratio for pure $Zn_3[Cu(CN)_4]_2$ is 1.50; x-ray fluorescence analysis gave a ratio of 1.56 for the

EXAMPLES 22-28

Bound catalysts were prepared from the complexes produced in Examples 19, 20 and 21 along with various catalyst supports or co-catalysts. These catalysts were prepared by mixing powders of the cyanide complexes with powders of the support or co-catalyst. The mixed powders were pelleted and chopped to 10/30 mesh.

These catalysts were activated with H$_2$/CO(1:1 molar) at 1 atmosphere pressure and 597° to 610° F. for about 16 hours.

Synthesis gas conversion activity was tested at 83 atm. pressure of H$_2$/CO(1:1 molar).

The reaction conditions and results are presented in Table 4, FIG. 1 contains the water gas shift equilibrium results.

TABLE 4

| Example | 22 | 23 | 24 | 25 |
|---|---|---|---|---|
| Catalyst | Zn$_3$[Cu(CN)$_4$]$_2$/Al$_2$O$_3$ | Cu$_{1.5}$Zn$_{1.5}$[Cu(CN)$_4$]$_2$/Al$_2$O$_3$ | Cu$_{1.5}$Zn$_{1.5}$[Cu(CN)$_4$]$_2$/HZSM-5/Al$_2$O$_3$ | Cu$_3$[Cu(CN)$_4$]$_2$/HZSM-5/Al$_2$O$_3$ |
| Proportions | 1/6.4 | 1/5 | 1/3.25/1.75 | 1/3.25/1.75 |
| Activation Procedure | | | | |
| Temperature °F. | 610 | 597 | 600 | 600 |
| Reaction Conditions | | | | |
| Time on stream, hrs. | 24 | 27.8 | 24.4 | 4.8 |
| WHSV (gCO/g Metal/hr.) | 3.07 | 2.02 | 2 | 2 |
| Temperature °F. | 511 | 508 | 501 | 501 |
| Pressure atm. | 83.4 | 82.7 | 83.4 | 83.0 |
| Conversion | | | | |
| Wt. % CO converted | 11.8 | 12.1 | 4.0 | .157 |
| Product Distribution (% Products) | | | | |
| Wt. % Hydrocarbon | .43 | .80 | .51 | .25 |
| Wt. % Dimethyl ether | 1.73 | 2.30 | .45 | — |
| Wt. % CH$_3$OH | 1.01 | 1.29 | .50 | — |
| Water Gas Shift | | | | |
| [CO$_2$] [H$_2$] / [CO] [H$_2$O] | 3.8 | — | .3 | — |

| Example | 26 | 27 | 28 |
|---|---|---|---|
| Catalyst | Cu$_{1.5}$Zn$_{1.5}$[Cu(CN)$_4$]$_2$ (Alone) | Zn$_3$[Cu(CN)$_4$]$_2$/Vycor | Zn$_3$[Cu(CN)$_4$]$_2$/Graphite |
| Proportions | — | 1/1.2 | 1/5 |
| Activation Procedure | | | |
| Temperature °F. | 600 | 609 | 600 |
| Reaction Conditions | | | |
| Time on stream, hrs. | 5 | 5.3 | 4 |
| WHSV (gCO/g Metal/hr.) | 31 | .8 | 2.1 |
| Temperature °F. | 502 | 505 | 504 |
| Pressure atm. | 84.0 | 82.7 | 82.2 |
| Conversion | | | |
| Wt. % CO converted | <.2 | <.2 | <.4 |
| Product Distribution (% Products) | | | |
| Wt. % Hydrocarbon | — | — | — |
| Wt. % Dimethyl ether | — | — | — |
| Wt. % CH$_3$OH | — | — | — |
| Water Gas Shift | | | |
| [CO$_2$] [H$_2$] / [CO] [H$_2$O] | — | — | — |

The data presented in the table illustrate the efficacy of the metal cyano cuprate catalysts in the conversion of synthesis gas to alcohols. FIG. 1 shows the increased water gas shift activity of the zinc cyano cuprate.

In addition, the necessity of alumina as a cocatalyst in the metal cyano cuprate catalysts is clearly seen by comparing Examples 26, 27, 28 with Examples 22–25. In this regard, alumina must be present in an effective amount, for example, in a ratio of alumina to metal cyano cuprate of from about 0.1/1 to 20/1 by weight.

We claim:

1. A method for the conversion of synthesis gas, which comprises a mixture of gaseous carbon oxides and hydrogen, to alcoholic products and hydrocarbons whereby water gas shift activity is increased, which comprises passing said synthesis gas at conversion conditions over a catayst comprising an effective amount of alumina and a metal cyano cuprate having the formula:

$$A_xB_y[Cu(CN)_4]$$

where the charge on the [Cu(CN)$_4$] anion of said cuprate is −3; where A and B are the same or different and are selected from the group consisting of zinc, iron, cobalt, nickel, ruthenium, thorium, rhodium, zirconium, hafnium, chromium, iridium, osmium, copper, rhenium, tungsten, titanium, manganese, molybdenum, lanthanum, cerium, uranium, hydrogen, sodium, potassium, rubidium, cesium, magnesium, calcium, strontium, and barium; and where x multiplied by the valence state of A plus y multiplied by the valence state of B equals +3.

2. The method of claim 1 wherein said catalyst further comprises a support or co-catalyst.

3. The method of claim 2 wherein said co-catalyst is ZSM-5.

4. The method of claim 1 wherein said synthesis gas conversion conditions comprise a temperature of from 400° F. to 1000° F. and a pressure of from 1 to 1000 atmospheres.

5. The method of claim 1 wherein said alumina is present in a ratio of alumina to metal cyano cuprate of from about 0.1/1 to 20/1 by weight.

6. The method of claim 1 wherein A and B are zinc.

7. The method of claim 1 wherein A is copper having valence state of +2 and B is zinc.

* * * * *

UNITED STATES PATENT AND TRADEMARK OFFICE
CERTIFICATE OF CORRECTION

PATENT NO. : 4,237,063
DATED : December 2, 1980
INVENTOR(S) : Weldon K. Bell, Clarence D. Chang It is certified that error appears in the above—identified patent and that said Letters Patent is hereby corrected as shown below:

Column 2, Line 7&8 - "Nevertheless to --Nonetheless--

Column 3, Line 22 - "and" to --und--

Column 4, Line 52 - "Ruthenium" should be --Rhenium--

Column 5, Line 7 - "union" should be --anion--

Column 13, Line 55 - delete second "described"

Column 14, Line 5 - "be" should be --bed--

Signed and Sealed this

Fourth Day of August 1981

[SEAL]

Attest:

Attesting Officer

GERALD J. MOSSINGHOFF

Commissioner of Patents and Trademarks